United States Patent
Lundstedt et al.

(10) Patent No.: US 8,227,502 B2
(45) Date of Patent: Jul. 24, 2012

(54) AMIDES ACTING ON THE ADENOSINE RECEPTORS

(75) Inventors: Torbjorn Lundstedt, Uppsala (SE); Elisabeth Seifert, Uppsala (SE); Per Lek, Uppsala (SE); Arne Boman, Uppsala (SE)

(73) Assignee: Anamar AB (SE)

( * ) Notice: Subject to any disclaimer, the term of this patent is extended or adjusted under 35 U.S.C. 154(b) by 287 days.

(21) Appl. No.: 12/514,634

(22) PCT Filed: Nov. 9, 2007

(86) PCT No.: PCT/EP2007/009721
§ 371 (c)(1),
(2), (4) Date: Dec. 10, 2009

(87) PCT Pub. No.: WO2008/058679
PCT Pub. Date: May 22, 2008

(65) Prior Publication Data
US 2010/0098629 A1    Apr. 22, 2010

(30) Foreign Application Priority Data
Nov. 15, 2006 (GB) .................................. 0622826.6

(51) Int. Cl.
A61K 31/404 (2006.01)
C07D 209/14 (2006.01)
(52) U.S. Cl. .......................... 514/418; 548/494; 548/504
(58) Field of Classification Search .................. None
See application file for complete search history.

(56) References Cited

U.S. PATENT DOCUMENTS

| | | | |
|---|---|---|---|
| 6,992,083 B2 | 1/2006 | Norcross | |
| 7,217,702 B2 | 5/2007 | Beauglehole et al. | |
| 7,285,548 B2 | 10/2007 | Flohr et al. | |
| 2007/0105821 A1 | 5/2007 | Wang et al. | |
| 2008/0176858 A1 | 7/2008 | Beauglehole et al. | |

FOREIGN PATENT DOCUMENTS

| | | |
|---|---|---|
| EP | 0420648 A2 | 4/1991 |
| WO | 2006028618 A1 | 3/2006 |
| WO | 2006091896 A2 | 8/2006 |
| WO | 2006091897 A2 | 8/2006 |
| WO | 2006091898 A2 | 8/2006 |

OTHER PUBLICATIONS

Cunha, et al. Curr Pharm Des., 14:1512 (2008).*
Hörig et al., J. Translational Med. 2:44 (2004).*
Bergnes, et al.;"Generation of an Ugi Library of Phosphate Mimic-Containing Compounds and Identification of Novel Dual Specific Phosphatase Inhibitors"; Bioorganic & Medicinal Chemistry Letters; 9; pp. 2849-2854; (1999).
Bonnaterre, et al.; "Rapid Access to Oxindoles by the Combined Use of an Ugi Four-Component Reaction and a Microwave-Assisted Intramolecular Buchwald-Hartwig Amidation Reaction"; Organic Letters; 8; pp. 4351-4354; (2006).
Zhang, et al.; "Identification of Inhibitors of Heparin-Growth Factor Interactions from Combinatorial Libraries for Four-Component Condensation Reactions"; Bioorganic & Medicinal Chemistry; 9; pp. 825-836; (2001).
International Search Report; International Application No. PCT/EP2007/009721; International Filing Date Nov. 9, 2007; Date of Mailing May 23, 2008; 4 pages.
Hasko, et al.; "Adenosine: An Endogenous Regulator of Innate Immunity"; Trends in Immunology; 25; pp. 33-39; (2004).
Montesinos, et al.; "Adenosine Promotes Wound Healing and Mediates Angiogenesis in Response to Tissue Injury Via Occupancy of A2A Receptors"; Americal Journal of Pathology; 160; pp. 2009-2018; (2002).
Peirce, et al.; "Selective A2A Adenosine Receptor Activation Reduces Skin Pressure Ulcer Formation and Inflammation"; Am J Physiol Heart Circ Physiol; 281; pp. H67-H74; (2001).
Varani, et al.; "Pharmacological and Biochemical Characterization of Purified A2A Adenosine Receptors in Human Platelet Membranes by [3H]-CGS 21680 Binding"; British Journal of Pharmacology; 117; pp. 1693-1701; (1996).

* cited by examiner

*Primary Examiner* — Kamal Saeed
*Assistant Examiner* — Michael Barker
(74) *Attorney, Agent, or Firm* — Cantor Colburn LLP

(57) ABSTRACT

There are described Compounds of formula (I) in which $R_3$ to $R_8$ are independently selected from hydrogen, halogen, trihaloalkyl, alkyl having 1, 2, 3, 4 or 5 carbon atoms, electron donor groups selected from alkoxy having 1, 2, 3, 4 or 5 carbon atoms, trihaloalkoxy, hydroxy or amino, electron acceptor groups selected from cyano, sulphonic, nitro, or amide; $R_1$ is an optionally substituted phenyl, benzyl or cyclohexyl group; $R_2$ is selected from amino, substituted amino or guanidino groups, Z is a saturated or unsaturated $C_{1-5}$ hydrocarbon chain, and salts thereof. A process for their preparation and compositions containing them are also described. The Compounds are either agonists or antagonists of a specific adenosine receptor or a number of adenosine receptors and have usefulness for the treatment of inflammation, arthritic conditions, rheumatoid arthritis, osteoarthritis, mental disorders, or for inducing central nerve regeneration.

14 Claims, 1 Drawing Sheet

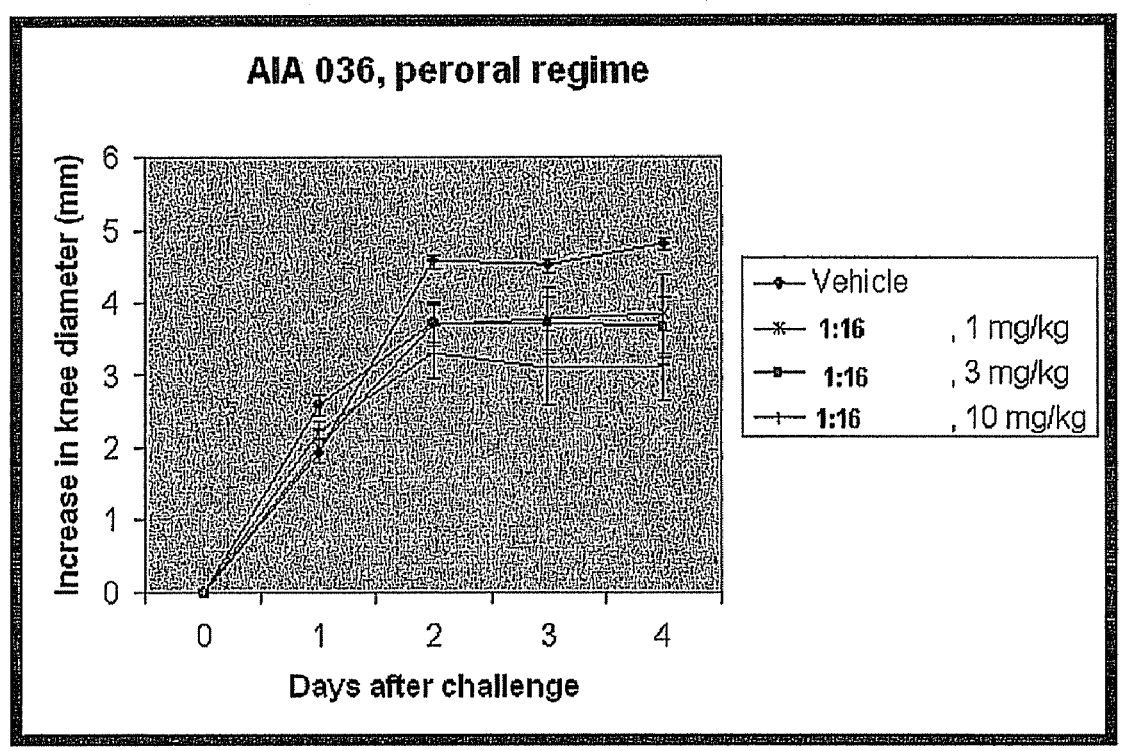

AMIDES ACTING ON THE ADENOSINE RECEPTORS

The present invention relates to novel amides and to the use of these amides for the treatment of inflammatory conditions, mental disorders and other diseases associated with the adenosine receptors.

An additional object of this invention is to provide compounds for therapeutic use, especially compounds having a therapeutic effect via the central nervous system (CNS). More particularly, we provide compounds having an antagonistic effect on the adenosine $A_{2A}$ receptor in mammals, including man.

BACKGROUND OF THE INVENTION

The present invention relates novel amides. Compounds of the present invention have been biologically tested towards the adenosine receptors and have surprisingly been shown to be capable of binding to the adenosine receptors, having activity in functional assays, as well as showing effect in vivo.

Compounds of the present invention are either agonists or antagonists of a specific adenosine receptor or a number of adenosine receptors, more specifically at the adenosine $A_{2A}$ receptor.

There are today a large amount of documents in the literature describing the present knowledge on adenosine and the adenosine receptors, a few examples are given below.

The adenosine receptors belong to the class of G-protein coupled receptors, also known as seven transmembrane receptors, which are all built from a single polypeptide forming 7 transmembrane domains. As the name indicates, adenosine is a naturally occurring endogenous ligand, which upon activation of the receptors initiates a signal transduction mechanism. There are currently four subtypes of adenosine receptor identified; $A_1$, $A_{2A}$, $A_{2B}$ and $A_3$. (Jacobson, et al., Adenosine receptors as therapeutic targets. *Nat Rev Drug Discov* 5, 247-64, 2006). All the receptors have a unique pharmacological profile and tissue distribution and there are growing evidence of their influence in a number of conditions such as cerebral and cardiac ischaemic diseases, sleeping disorders, cancer, immune and inflammatory disorders, Alzheimer's disease, Parkinson's disease Huntingtons's disease, neuroprotection, schizophrenia, anxiety, pain, respiration deficits, depression, drug abuse (amphetamine, cocaine, opioids, ethanol, nicotine, cannabinoids), or against asthma, allergic responses, hypoxia, ischaemia, seizure, and substance abuse, sedatives, muscle relaxants, antipsychotics, antiepileptics, anticonvulsants and cardiaprotective agents for disorders such as coronary artery disease and heart failure. The adenosine $A_2$, has been shown to have a crucial role in the modulation of prolonged systemic inflammatory responses (Ohta, et al., Role of G-protein-coupled adenosine receptors in downregulation of inflammation and protection from tissue damage. *Nature* 414, 916-20, 2001). More specifically the $A_{2A}$ receptor has been investigated in vivo for treatment of sepsis (Sullivan, et al., $A_2$, adenosine receptor activation improves survival in mouse models of endotoxemia and sepsis. J Infect D is 189, 1897-904, 2004), inflammatory bowel disease (Odashima, et al. Activation of $A_{2A}$ adenosine receptor attenuates intestinal inflammation in animal models of inflammatory bowel disease. *Gastroenterology* 129, 26-33, 2005), reducing skin pressure, ulcer formation and inflammation (Peirce, et al., Selective $A_{2A}$ adenosine receptor activation reduces skin pressure ulcer formation and inflammation. *Am J Physiol Heart Circ Physiol* 281, H67-74, 2001), improved wound healing (Montesinos, et al., Adenosine promotes wound healing and mediates angiogenesis in response to tissue injury via occupancy of $A_{2A}$ receptors. *Am J Pathol* 160, 2009-18, 2002), as well as been implicated as a route for arthritis treatment (Hasko, et al., Adenosine: an endogenous regulator of innate immunity, *Trends Immunol* 25, 33-9, 2004).

Hence, after more than three decades of research of the adenosine receptors, a variety of physiological actions have been identified that are thought to be mediated by the distinct subtypes of each receptor. In many cases, however, it is still not entirely clear which of the subtypes that is responsible for the effect The compounds in the present application are structurally different from the previously published adenosine agonists and antagonists, e.g. WO06091936, WO06091898, WO06091897, WO06091896, WO05097140, WO04063177, WO06028618, WO030186926, WO04105755, WO04063177, and reviewed in Jacobson et al., (Adenosine as receptor targets, Nature reviews, 5, 247-264, 2006). Most of the applications are related to modifications of adenosine itself, which makes the observed effects of the novel compounds are unexpected.

DESCRIPTION OF THE INVENTION

One aspect of the present invention is therefore to provide low molecular weight compounds showing activity on adenosine receptors. A further aspect is to provide compounds which may be taken up after oral administration and which penetrate well through the blood brain barrier.

In one aspect, the present invention provides novel compounds of the general formula (I):

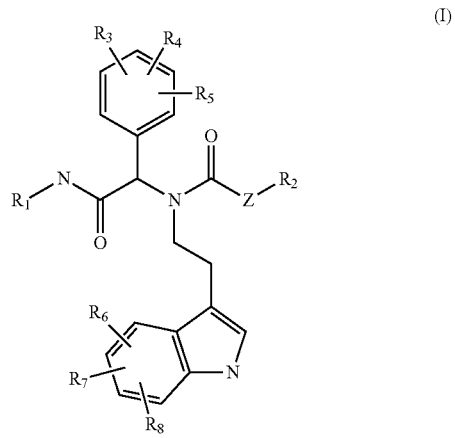

and tautomers, isomers, diastereomers, enantiomers, and mixtures thereof wherein $R_1$ is selected from;

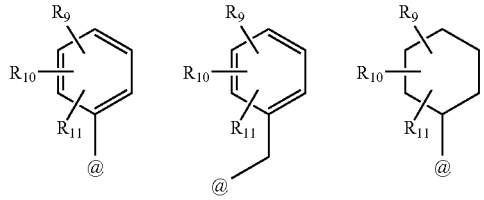

In which @ denotes the position where $R_1$ is attached to the nitrogen atom;

wherein Z is a saturated or unsaturated, straight or branched chain acyclic hydrocarbon group having 1, 2, 3, 4 or 5, preferably 1 or 2, and most preferably 2 carbon atoms;

$R_2$ is selected from amino, substituted amino, such as alkylamino or dialkylamino, e.g. methylamino, dimethylamino, ethylamino, diethylamino, or a guanidino group;

$R_3$, $R_4$ and $R_5$, which may be the same or different, are independently selected from hydrogen, halogen, trihaloalkyl, alkyl having 1, 2, 3, 4 or 5 carbon atoms, electron donor groups selected from alkoxy having 1, 2, 3, 4 or 5 carbon atoms, trihaloalkoxy, hydroxy or amino, and electron acceptor groups selected from cyano, sulphonic, nitro, or amide;

$R_6$, $R_7$ and $R_8$, which may be the same or different, are independently selected from hydrogen, halogen, trihaloalkyl, alkyl having 1, 2, 3, 4 or 5 carbon atoms, electron donor groups selected from alkoxy having 1, 2, 3, 4 or 5 carbon atoms, trihaloalkoxy, hydroxy or amino, and electron acceptor groups selected from cyano, sulphonic, nitro, or amide;

and $R_9$, $R_{10}$ and $R_{11}$, which may be the same or different, are independently selected from hydrogen, halogen, trihaloalkyl, alkyl having 1, 2, 3, 4 or 5 carbon atoms, electron donor groups selected from alkoxy having 1, 2, 3, 4 or 5 carbon atoms, trihaloalkoxy, hydroxy or amino, and electron acceptor groups selected from cyano, sulphonic, nitro, or amide;

and salts thereof, particularly physiologically acceptable salts thereof with inorganic or organic acids.

The term alkoxy also includes fused alkoxy, e.g. a methylenedioxy or ethylenedioxy group such as might be formed by two of $R_3$, $R_4$ and $R_5$, $R_6$, $R_7$ and $R_8$, and $R_9$, $R_{10}$ and $R_{11}$ when present on the ring systems in formula (I).

When used in the foregoing definitions, the term alkyl includes straight or branched chain hydrocarbon groups; the term alkoxy includes straight or branched chain alkoxy groups; and the term halogen includes fluoro, chloro, bromo or iodo.

Preferably, the "alkyl having 1, 2, 3, 4 or 5 carbon atoms" is a lower alkyl such as methyl, ethyl, propyl or iso-propyl.

Preferably, the "alkoxy having 1, 2, 3, 4 or 5 carbon atoms" is a lower alkoxy such as methoxy, ethoxy, propoxy, iso-propoxy or t-butoxy.

Preferably, the halogen is fluoro, chloro or bromo, and most preferably bromo.

Preferably, the trihaloalkyl is a trifluoroalkyl group, such as trifluoromethyl, trifluoroethyl, trifluoropropyl or trifluoroisopropyl. The trihaloalkoxy group is preferably a trifluoroalkoxy group, particularly trifluoromethoxy.

Preferred are compounds in which at least one of $R_3$, $R_4$ and $R_5$ is a halogen atom or alkyl group. Further preferred are compounds in which the substitution pattern of $R_3$, $R_4$ and $R_5$ is in the 2- and/or 4- and/or 6-positions of the phenyl ring relative to the point of attachment of the phenyl ring to the background chain. Compounds comprising a 2-halo, 2,4-dihalo and 2-alkyl substituents are preferred. Preferred substituents include fluoro, chloro, bromo and methyl.

The compounds of formula (I) have basic properties and, consequently, they may be converted to their therapeutically active acid addition salts by treatment with physiologically acceptable acids, e.g. inorganic acids such as hydrochloric, hydrobromic, sulphuric, nitric and phosphoric acid, or organic acids such as acetic, trifluoroacetic, propanoic, glycolic, lactic, malonic, succinic, fumaric, tartaric, citric and palmoic acid.

Conversely, the salt form may be converted into the free base form by treatment with alkali.

The present invention relates also to racemates of the compounds of general formula (I). However, the invention also includes the individual diastereomeric pairs of antipodes or mixtures thereof which are obtained if there is more than one chiral element in the compounds of general formula (I) as well as the individual optically active enantiomers of which the above-mentioned racemates are made up.

The compounds of formula (I) acting as antagonists towards the adenosine $A_2$ receptor and/or their pharmaceutically acceptable salts have valuable pharmacological properties, making them useful for the treatment of disorders in the CNS system such as Parkinson's disease, anxiety, depression, drugs abuse, schizophrenia, Alzheimer's and Huntingdon's diseases.

The compounds of formula (I) acting as agonists to the adenosine $A_2$ receptor and/or their pharmaceutically acceptable salts have valuable pharmacological properties, making them useful for the treatment of inflammation such as rheumatoid arthritis, psoriatic arthritis, systemic sclerosis, polymyalgia rheumatica, and mixed connective tissue disease. Included within this is also arthritis, including arthritis of unknown origin as well as other inflammatory conditions.

Compounds of the invention may be used for the treatment and diagnosis of diseases, disorders and/or pathological conditions in an animal, in particular in man.

The present invention also relates to a pro-drug which, upon administration to an animal or a human, is converted to a compound of the invention. Pro-drugs of the compounds of formula (I) and their pharmacologically acceptable salts may be used for the same purposes as described in this specification for the compounds of the invention, as well as is disclosed in the Examples given below.

The invention also relates to methods for the manufacture of and to pharmaceutical preparations comprising one or more of the compounds of the invention in admixture with acceptable carriers, diluents or excipients, as well as to their uses for various medical and veterinary practices related to adenosine receptors.

Methods of Preparation

In another aspect of the aspect, the compounds of the invention may be made according to the general synthetic scheme shown below:

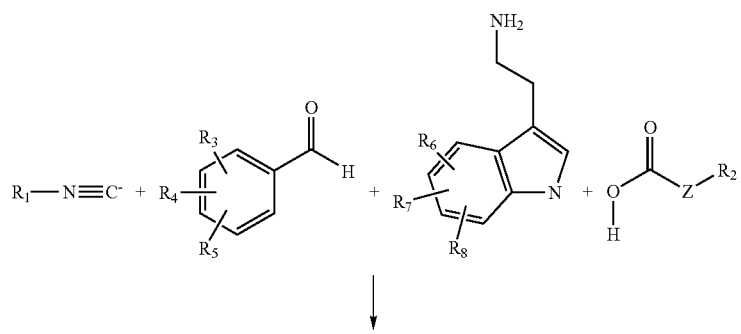

-continued

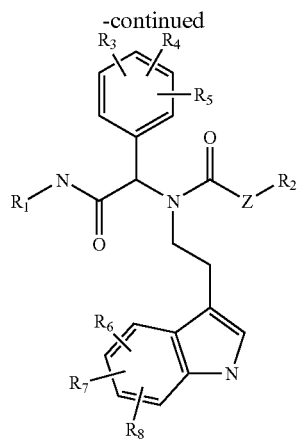

wherein $R_1$, $R_2$, $R_3$, $R_4$, $R_5$, $R_6$, $R_7$, $R_8$ and Z are as previously defined.

The compounds exemplified below can be prepared by a general procedure using standard Ugi four-component reaction conditions (see for example Ugi, I. *Angew. Chem. Int. Ed. Engl.*, 1982, 21, 810).

By way of example, the carboxylic acid (protected elsewhere if desired), the free amine, the aldehyde and the isocyanide shown in the scheme above are dissolved in a lower alkanol, e.g. methanol. The reaction mixture is stirred at e.g. room temperature until the reaction is complete, which typically may take one or more days. Alternatively, the mixture can be heated, e.g. using microwaves, by which the reaction times are significantly reduced. Under these circumstances, reaction within an hour may be achieved (see for example Hoel, A. et al. *Tetrahedron Lett.*, 1999, 40, 3941-3944). The product may be purified by conventional techniques, e.g. by chromatography.

Optical isomers can be separated using several methods well known in the art, such as by using chiral resolving agents, i.e. by generating diasteromeric salts of amines and a carboxylic acid, which results in the diastereomers being able to be separated from each other and the pure enantiomer obtained by simple deprotonation. An alternative or additional method of separation is to use chiral column chromatography.

In an embodiment, the compounds of formula (I) further comprise a label, perferable wherein the label is a radioactive label or a toxic agent.

EXAMPLES

Compounds of the general formula (I) may be prepared by the following methods.

The following Examples are intended to illustrate but not to limit the scope of the invention, although the compounds named are of particular interest for the intended purposes. These compounds have been designated by a number code, a:b, where a means the number of the Example wherein the preparation of the compound is described, and b refers to the order of the compound prepared according to that Example. Thus Example 1:2 means the second compound prepared analogously according to the method described in Example 1.

The structures of the compounds were confirmed by IR, NMR, MS and elementary analysis. When melting points are given, these are uncorrected.

Example 1:1

3-Bromo-benzaldehyde (1 eq), 2-(1H-indol-3-yl)-ethylamine (1 eq), N-Boc-3-aminopropanoic acid (1 eq) and cyclohexylisocyanide (1 eq) were dissolved in 15 ml methanol. The reaction was stirred at room temperature for 18 h by which time a white precipitate formed. The solvent was evaporated and the precipitate was washed with methanol to give the crude product in 78% yield. The Boc group was removed by heating the crude product at 40° C. in a mixture of HCl/methanol for one hour. Chromatography on silica with $CH_2Cl_2$:MeOH 6:1 gave the pure product. Melting point 209° C.

Compound list

| No. | Compound name | M.p. (deg. C.) | salt |
|---|---|---|---|
| 1:1 | 3-Amino-N-[(3-bromo-phenyl)-cyclohexyl-carbamoyl-methyl]-N-[2-(1H-indol-3-yl)-ethyl]-propionamide | 209 | HCl |
| 1:2 | 3-Amino-N-[(2-bromo-phenyl)-cyclohexylcarbamoyl-methyl]-N-[2-(1H-indol-3-yl)-ethyl]-propionamide | 242 | HCl |
| 1:3 | 3-Amino-N-[(4-bromo-phenyl)-cyclohexylcarbamoyl-methyl]-N-[2-(1H-indol-3-yl)-ethyl]-propionamide | 228 | HCl |
| 1:4 | 3-Amino-N-[cyclohexylcarbamoyl-(2,4-dibromo-phenyl)-methyl]-N-[2-(1H-indol-3-yl)-ethyl]-propionamide | 246 | HCl |
| 1:5 | 3-Amino-N-[cyclohexylcarbamoyl-(2,5-dibromo-phenyl)-methyl]-N-[2-(1H-indol-3-yl)-ethyl]-propionamide | 266 | HCl |
| 1:6 | 3-Amino-N-[benzylcarbamoyl-(2-bromo-phenyl)-methyl]-N-[2-(1H-indol- 3-yl)-ethyl]-propionamide hydrochloride | 156-158 | HCl |
| 1:7 | N-[Benzylcarbamoyl-(2-bromo-phenyl)-methyl]-3-dimethylamino-N-[2-(1H-indol-3-yl)-ethyl]-propionamide acetamide | 180 | |
| 1:8 | N-[Benzylcarbamoyl-(2-bromo-phenyl)-methyl]-N-[2-(5-bromo-1H-indol-3-yl)-ethyl]-3-dimethylamino-propionamide | 138-141 | |
| 1:9 | 3-Amino-N-[benzylcarbamoyl-(2,4-dibromo-phenyl)-methyl]-N-[2-(1H-indol-3-yl)-ethyl]-propionamide | 203-205 | HCl |
| 1:10 | 3-Amino-N-[benzylcarbamoyl-(2,5-dibromo-phenyl)-methyl]-N-[2-(1H-indol-3-yl)-ethyl]-propionamide | 220 | HCl |
| 1:11 | 3-Amino-N-[benzylcarbamoyl-(3-bromo-phenyl)-methyl]-N-[2-(1H-indol-3-yl)-ethyl]-propionamide | 195 | HCl |

Compound list

| No. | Compound name | M.p. (deg. C.) | salt |
|---|---|---|---|
| 1:12 | 3-Amino-N-[benzylcarbamoyl-(4-bromo-phenyl)-methyl]-N-[2-(1H-indol-3-yl)-ethyl]-propionamide | 136-138 | HCl |
| 1:13 | 3-Amino-N-[(2-bromo-phenyl)-phenylcarbamoyl-methyl]-N-[2-(1H-indol-3-yl)-ethyl]-propionamide | foam | CF₃COOH |
| 1:14 | 3-Amino-N-[(3-bromo-phenyl)-phenylcarbamoyl-methyl]-N-[2-(1H-indol-3-yl)-ethyl]-propionamide | foam | CF₃COOH |
| 1:15 | 3-Amino-N-[(4-bromo-phenyl)-phenylcarbamoyl-methyl]-N-[2-(1H-indol-3-yl)-ethyl]-propionamide | foam | CF₃COOH |
| 1:16 | 3-Amino-N-[(2,4-dibromo-phenyl)-phenylcarbamoyl-methyl]-N-[2-(1H-indol-3-yl)-ethyl]-propionamide | foam | CF₃COOH |
| 1:17 | 3-Amino-N-[(2,5-dibromo-phenyl)-phenylcarbamoyl-methyl]-N-[2-(1H-indol-3-yl)-ethyl]-propionamide | foam | CF₃COOH |
| 1:18 | N-[(2-Chloro-phenyl)-phenylcarbamoyl-methyl]-N-[2-(6-fluoro-1-indol-3-yl)-ethyl]-3-guanidino-propionamide | 166-167 | HCl |
| 1:19 | 3-Amino-N-[(4-fluoro-phenylcarbamoyl)-(4-trifluoromethyl-phenyl)-methyl]-N-[2-(5-methoxy-1H-indol-3-yl)-ethyl]-propionamide | | |
| 1:20 | N-[(4-Chloro-3-nitro-phenyl)-phenylcarbamoyl-methyl]-3-guanidino-N-[2-(6-methoxy-1H-indol-3-yl)-ethyl]-propionamide | | |
| 1:21 | 3-Diethylamino-N-[(3-fluoro-4-methoxy-phenyl)-(4-fluoro-phenylcarbamoyl)-methyl]-N-[2-(5-methyl-1H-indol-3-yl)-ethyl]- | | |
| 1:22 | 3-Amino-N-[(2-chloro-4-fluoro-phenyl)-(4-fluoro-phenylcarbamoyl)-methyl]-N-[2-(6-fluoro-1H-indol-3-yl)-ethyl]-propionamide | | |
| 1:23 | 3-Amino-N-[(2-chloro-phenyl)-phenylcarbamoyl-methyl]-N-[2-(6-fluoro-1H-indol-3-yl)-ethyl]-propionamide | | |
| 1:24 | N-[(4-Fluoro-phenylcarbamoyl)-(4-trifluoromethyl-phenyl)-methyl]-3-guanidino-N-[2-(5-methoxy-1H-indol-3-yl)-ethyl]-propionamide | | |
| 1:25 | 3-Amino-N-[(4-chloro-3-nitro-phenyl)-phenylcarbamoyl-methyl]-N-[2-(6-methoxy-1H-indol-3-yl)-ethyl]-propionamide | | |
| 1:26 | N-[(2-Chloro-4-fluoro-phenyl)-(4-fluoro-phenylcarbamoyl)-methyl]-N-[2-(6-fluoro-1H-indol-3-yl)-ethyl]-3-guanidino-propionamide | | |
| 1:27 | N-[(2-Chloro-4-fluoro-phenyl)-(4-fluoro-phenylcarbamoyl)-methyl]-3-guanidino-N-[2-(5-methoxy-1H-indol-3-yl)-ethyl]-propionamide | | |
| 1:28 | N-[(2-Chloro-4-fluoro-phenyl)-(4-fluoro-phenylcarbamoyl)-methyl]-3-guanidino-N-[2-(5-methoxy-1H-indol-3-yl)-ethyl]-propionamide | | |
| 1:29 | 3-Amino-N-[(2-chloro-4-fluoro-phenyl)-(4-fluoro-phenylcarbamoyl)-methyl]-N-[2-(5-methoxy-1H-indol-3-yl)-ethyl]-propionamide | | |
| 1:30 | N-[2-(6-Fluoro-1H-indol-3-yl)-ethyl]-N-[(4-fluoro-phenylcarbamoyl)-(4-trifluoromethyl-phenyl)-methyl]-3-guanidino-propionamide | | |
| 1:31 | 3-Amino-N-[2-(6-fluoro-1H-indol-3-yl)-ethyl]-N-[(4-fluoro-phenylcarbamoyl)-(4-trifluoromethyl-phenyl)-methyl]-propionamide | | |
| 1:32 | 3-Amino-N-[(2-chloro-phenyl)-phenylcarbamoyl-methyl]-N-[2-(6-methoxy-1H-indol-3-yl)-ethyl]-propionamide | | |
| 1:33 | N-[(2-Chloro-phenyl)-phenylcarbamoyl-methyl]-3-guanidino-N-[2-(6-methoxy-1H-indol-3-yl)-ethyl]-propionamide | | |
| 1:34 | 3-Amino-N-[(4-chloro-3-nitro-phenyl)-phenylcarbamoyl-methyl]-N-[2-(6-fluoro-1H-indol-3-yl)-ethyl]-propionamide | | |
| 1:35 | N-[(4-Chloro-3-nitro-phenyl)-phenylcarbamoyl-methyl]-N-[2-(6-fluoro-1H-indol-3-yl)-ethyl]-3-guanidino-propionamide | | |
| 1:36 | N-[(2-Bromo-phenyl)-phenylcarbamoyl-methyl]-3-guanidino-N-[2-(1H-indol-3-yl)-ethyl]-propionamide | | |
| 1:37 | 3-Amino-N-[(2-chloro-phenyl)-penylcarbamoyl-methyl]-N-[2-(1Hindol-3-yl)-ethyl]-propionamide | | |
| 1:38 | N-[(2-Chloro-phenyl)-phenylcarbamoyl-methyl]-3-guanidino-N-[2-(1H-indol-3-yl)-ethyl]-propionamide | | |
| 1:39 | 3-Amino-N-[(2-bromo-phenyl)-(4-fluoro-phenylcarbamoyl)-methyl]-N-[2-(1H-indol-3-yl)-ethyl]-propionamide | | |
| 1:40 | N-[(2-Bromo-phenyl)-(4-fluoro-phenyl-carbamoyl)-methyl]-3-guanidino-N-[2-(1H-indol-3-yl)-ethyl]-propionamide | | |
| 1:41 | N-[(2,4-Dibromo-phenyl)-phenylcarbamoyl-methyl]-3-guanidino-N-[2-(1H-indol-3-yl)-ethyl]-propionamide | | |
| 1:42 | 3-Amino-N-[(2-chloro-4-fluoro-phenyl)-phenylcarbamoyl-methyl]-N-[2-(1H-indol-3-yl)-ethyl]-propionamide | | |
| 1:43 | N-[(2-Chloro-4-fluoro-phenyl)-phenyl-carbamoyl-methyl]-3-guanidino-N-[2-(1H-indol-3-yl)-ethyl]-propionamide | | |
| 1:44 | 3-Amino-N-[(2,4-dibromo-phenyl)-(4-fluoro-phenylcarbamoyl)-methyl]-N-[2-(1H-indol-3-yl)-ethyl]-propionamide | | |
| 1:45 | N-[(2,4-Dibromo-phenyl)-(4-fluoro-phenyl-carbamoyl)-methyl]-3-guanidino-N-[2-(1H-indol-3-yl)-ethyl]-propionamide | | |
| 1:46 | N-[(4-Bromo-phenyl)-phenylcarbamoyl-methyl]-3-guanidino-N-[2-(1H-indol-3-yl)-ethyl]-propionamide | | |
| 1:47 | 3-Amino-N-[(4-chloro-phenyl)-phenyl-carbamoyl-methyl]-N-[2-(1H-indol-3-yl)-ethyl]-propionamide | | |
| 1:48 | N-[(4-Chloro-phenyl)-phenylcarbamoyl-methyl]-3-guanidino-N-[2-(1H-indol-3-yl)-ethyl]-propionamide | | |
| 1:49 | 3-Amino-N-[(4-chloro-phenyl)-(4-chloro-phenylcarbamoyl)-methyl]-N-[2-(1H-indol-3-yl)-ethyl]-propionamide | | |
| 1:50 | N-[(4-Chloro-phenyl)-(4-chloro-phenyl-carbamoyl)-methyl]-3-guanidino-N-[2-(1H-indol-3-yl)-ethyl]-propionamide | | |
| 1:51 | 3-Amino-N-[(4-chloro-phenyl)-phenyl-carbamoyl-methyl]-N-[2-(5-methoxy-1H-indol-3-yl)-ethyl]-propionamide | | |
| 1:52 | N-[(4-Chloro-phenyl)-phenylcarbamoyl-methyl]-3-guanidino-N-[2-(5-methoxy-1H-indol-3-yl)-ethyl]-propionamide | | |
| 1:53 | 3-Amino-N-[2-(1H-indol-3-yl)-ethyl]-N-(phenylcarbamoyl-o-tolyl-methyl)-propionamide | foam | CF₃COOH |
| 1:54 | 4-Amino-N-[benzylcarbamoyl-(2-bromo-phenyl)-methyl]-N-(4-trifluoromethoxy-benzyl)butyramide | 127-128 | HCl |
| 1:55 | 3-Diethylamino-N-[(3-fluoro-4-methoxy-phenyl)-(4-fluoro-phenylcarbamoyl)-methyl]-N-[2-(5-methyl-1H-indol-3-yl)-ethyl]-propionamide | 85-87 | AcOH |
| 1:56 | 3-Guanidino-N-[2-(1H-indol-3-yl)-ethyl]-N-(phenylcarbamoyl-o-tolyl-methyl)-propionamide | | |
| 1:57 | 3-Guanidino-N-[2-(1H-indol-3-yl)-ethyl]-N-[(2-methoxy-phenyl)-phenylcarbamoyl-methyl]-propionamide | | |
| 1:58 | 3-Guanidino-N-[2-(1H-indol-3-yl)-ethyl]-N-[(4-methoxy-2-methyl-phenyl)-phenylcarbamoyl-methyl]-propionamide | | |
| 1:59 | 3-Guanidino-N-[2-(1H-indol-3-yl)-ethyl]-N-[(4-methoxy-2,5-dimethyl-phenyl)-phenylcarbamoyl-methyl]-propionamide | | |

-continued

Compound list

| No. | Compound name | M.p. (deg. C.) salt |
|---|---|---|
| 1:60 | 3-Amino-N-[2-(1H-indol-3-yl)-ethyl]-N-[(2-methoxy-phenyl)phenylcarbamoyl-methyl]-propionamide | |
| 1:61 | 3-Amino-N-[2-(1H-indol-3-yl)-ethyl]-N-[(4-methoxy-2-methyl-phenyl)phenylcarbamoyl-methyl]-propionamide | |
| 1:62 | 3-Guanidino-N-[2-(1H-indol-3-yl)-ethyl]-N-[(4-methoxy-2,5-dimethyl-phenyl)-phenylcarbamoyl-methyl]-propionamide | |

IN VITRO EXAMPLES

Example 2

Affinity to Adenosine

This Example illustrates the potency of compounds of formula (I) and their therapeutically active acid addition salts.

The affinity and functionality towards the adenosine $A_{2A}$ receptor was essentially performed as described by Varani et al. (Varani, Pharmacological and biochemical characterization of purified $A_{2A}$ adenosine receptors in human platelet membranes by [$^3$H]CGS21680 binding, Br. J. Pharmacol. 117:1693-1701, 1996), Table 1.

TABLE 1

Affinity for adenosine $A_{2A}$.

| Compound No | IC50 (µM) | Ki (µM) |
|---|---|---|
| 1:02 | | 1 |
| 1:04 | 2.84 | 1.6 |
| 1:09 | 5.11 | 2.87 |
| 1:13 | | 0.06 |
| 1:15 | 0.243 | 0.136 |
| 1:16 | 0.0311 | 0.0175 |

Example 3

Synovial fibroblasts

Study design: From rats with antigen induced arthritis, the hyperproliferative synovium, pannus, was taken from the inflamed knee day four after disease onset. The pannus tissue was cut to small pieces in PBS with PEST (100 IU penicillin, 100 µg/ml streptomycin) and Fungizone (2.5 µg/ml) (all from InVitrogen, Sweden), before incubation in collagenase (400 U/ml, Worthington, USA) for 3 hours at 37° C., 5% CO2. Cells were centrifugated (8 min., rt, 1100 rpm.) and suspended in RPMI 1640 supplemented with 10% FCS (InVitrogen, Sweden), PEST and Fungizone and seeded in a 25 cm² flask at 37° C., 5% $CO_2$. The following day, cells were rinsed once with medium and further incubated. When confluent, cells were trypsinated for 1 min (0.25% trypsin with EDTA, InVitrogen, Sweden) counted and seeded in 96 well plates, 10000 cells/well/200 µl.

After 24 hours, the medium was changed and the cells were stimulated with human recombinant IL-1a, 50 ng/ml (Roche, Sweden). The compounds were tested in triplets in the concentration interval 5-1000 nM. After 72 hour incubation at 37° C., 5% $CO_2$, the medium was collected for measurement of NO (Griess reaction) and IL-6 was analyzed by an ELISA, according to the manufacturer's instructions (BD Biosciences, USA).

Example 4

Carthage Explants

The effect of the compounds on NO release in IL-1 stimulated cartilage was measured as described below.

A skinned bovine nose (from cows 18-24 months old) was collected at Hörby slaughter house (Team Ugglarp, Sweden). The septum inside the nose was cut out and the mucosa and the perichondrium was removed before the cartilage was placed in PBS with PEST (100 IU penicillin, 100 mg/ml streptomycin) and 2.5 ug/ml Fungizone (all from Invitrogen, Sweden) for 2 hours at rt. Two mm pieces were punched out of the cartilage. Each piece was placed in a 24-well cell culture plate (Falcon, Sweden) containing 1 ml cell culture medium, HAMs F12 (Invitrogen, Sweden) supplemented with 10 µg/ml BSA, 25 mg/ml ascorbate (both from Sigma, Sweden), PEST (100 IU penicillin, 100 mg/ml streptomycin) and 2.5 ug/ml Fungizone. After 24 hours, the medium was changed and the cartilage pieces were stimulated with human recombinant IL-1a, 10 ng/ml (Roche, Sweden). The test compounds were tested in triplets at a suitable concentration 5-1000 nM.

The cartilage tissue was incubated for another six days, mediums were exchanged every third day. On each occasion the mediums were collected for measurement of NO (Griess reaction).

Example 5

Anti Inflammatory Effects

Control

Female BALB/c mice (weight 20-22 g) were sensitized by treatment of the shaved abdomen with 30 µl of 0.5% 2,4-dinitrofluorobenzene (DNFB). After 4 days they were challenged with 10 µl of 0.3% DNFB to the paw. The unchallenged mice paws served as a control. Twenty-four hours after the last challenge, the differences in paws weight were determined as an indicator of the inflammation (paw edema).

Prednisolone Control

Mice were treated as the control but were additionally injected intraperitoneally (i.p.) or (s.c.) prednisolone (20 mg/kg) two hours before sensitization (day 0) and the same dose was administered repeatedly after sensitization during four consecutive days. The paw edema inhibition was measured as described above.

Study of New Compounds

Mice were treated as the control but were additionally injected i.p. or (s.c.) with various doses (0.05, 0.15 or 0.25, 0.375, 0.5, 0.75 and in later studies also 1.5, 3 and occasionally 6 mg/kg) of each compounds two hours before sensitization (day 0) and the same dose was administered repeatedly after sensitization during four consecutive days. The paw edema inhibition as described above. Groups containing at least 10 mice each were used for all experiments.

Blood analysis was carried out using the QBC® Autoread™ Plus & QBC® Accutube System (Becton Dickinson). In all cases blood samples were collected twenty-four hours after the last challenge.

Example 6

Antigen Induced Arthritis (AIA)

Antigen Induced Arthritis (AIA) in the rat is a well reproducible monoarthritis model. An intraarticular injection of the antigen methylated bovine serum albumin (mBSA) in the knee joint in sensitised animals induces an inflammatory response. The formation of pannus tissue, which invades the synovium, spreads over the articular cartilage and grows into the bone, leading to tissue erosion and remodeling.

AIA responds well to compounds used for standard clinical treatment of human arthritis. Therefore this model is appropriate for the evaluation of the effects of new compounds on joint inflammation and cartilage/bone degradation. The test compounds can be administered locally or systemically. The features of the arthritis can be followed and evaluated by measuring knee joint swelling, by functional scoring and histological analysis. Since it is a monoarthritis model, the level of inflammatory serum markers may be difficult to detect. The AIA model also serves as a source for the production of synoviocytes for in vitro culturing, in order to gain further insight in the synovial matrix composition and for drug screening purposes.

In Antigen induced arthritis—for the effect on knee diameter of Compound 1:16 after per oral administration—see FIG. 1.

1:16 reduced the swelling of the knee after antigen induced arthritis.

Example 7

Collagen-Induced Arthritis (CIA)

Collagen-induced arthritis (CIA) in the mouse is the most common experimental model for rheumatoid arthritis, with several features in common with the human disease. Autologous or heterologous collagen type II (CII) emulsified in Freund's Complete Adjuvant induces a polyarthritis, with edema of the synovial tissue, synovial cell proliferation, inflammatory cell infiltration and erosions of cartilage and bone. The test compounds should be administered systemically. The features of polyarthritis can be evaluated by scoring the signs of arthritis, histological analysis and by measurements of serum biomarkers. The bone mineral content and density may also be analysed by mouse densitometry (PIXIMUS).

Suitable forms of pharmaceutical preparation for administration include for example tablets, capsules, solutions, syrups, or emulsions. The content of the pharmaceutically effective compound(s) in each case should desirably be in the range from 0.1 to 5 wt. %, of the total composition.

The preparations may be administered orally in the form of a tablet, as a powder, as a powder in a capsule (e.g. a hard gelatine capsule), as a solution or suspension.

It is preferable if the compounds of formula (I) are administered orally. Suitable tablets may be obtained, for example, by mixing the active substance(s) with known carriers, diluents or excipients, such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may suitably be prepared by coating cores produced similarly to the tablets with substances normally used for tablet coatings, for example collidone or shellac, gum arabic, talc, titanium dioxide or sugar. The tablet coating may consist of a number of layers to achieve delayed release, possibly using the excipients mentioned above for the tablets.

Capsules containing one or more active substances or combinations of active substances may for example be prepared by mixing the active substances with inert carriers such as lactose or sorbitol and packing them into gelatine capsules. Suppositories may be made for example by mixing with carriers provided for this purpose, such as neutral fats or polyethyleneglycol or the derivatives thereof.

Syrups containing the active substances or combinations thereof according to the invention may additionally contain a sweetener such as saccharin, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may contain, in addition to the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions, the active substances may be combined with various flavour enhancers or colourings in addition to the excipients mentioned above.

A solution for parenteral administration by injection of a water-soluble pharmaceutically acceptable acid addition salt of the active substance can be prepared in an aqueous solution, preferably in a concentration of 0.1% to about 5% by weight. These solutions may also contain stabilising agents and/or buffering agents.

Example 8

Formulations

Example of a Preparation Comprising a Capsule

|  | Per capsule |
| --- | --- |
| Active ingredient, as salt | 5 mg |
| Lactose | 250 mg |
| Starch | 120 mg |
| Magnesium stearate | 5 mg |
| Total up to | 380 mg |

In cases higher amounts of active ingredient are required, the amount of lactose used may be reduced.

Example of a Suitable Tablet Formulation.

| | Per tablet |
|---|---|
| Active ingredient, as salt | 5 mg |
| Potato starch | 238 mg |
| Colloidal Silica | 10 mg |
| Talc | 20 mg |
| Magnesium stearate | 2 mg |
| 5% aqueous solution of gelatine | 25 mg |
| Total up to | 300 mg |

The invention claimed is:

1. A compound of general formula (I)

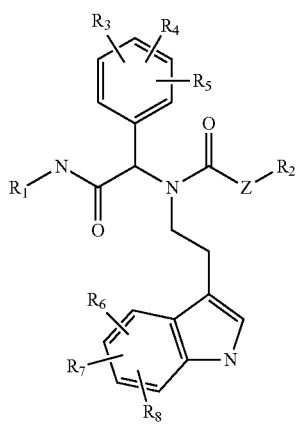

and tautomers, diastereomers, enantiomers, and mixtures thereof, wherein $R_1$ is selected from

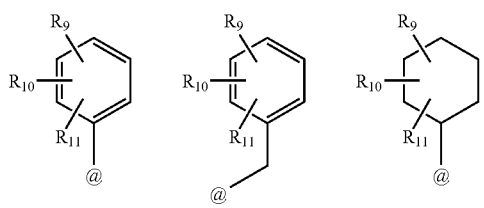

in which @ denotes the position where $R_1$ is attached to the nitrogen atom;

Z is a saturated or unsaturated, straight or branched chain acyclic hydrocarbon group having 1, 2, 3, 4 or 5 carbon atoms;

$R_2$ is selected from an amino, alkylamino, dialkylamino, or a guanidine group;

$R_3$, $R_4$ and $R_5$ are the same or different and are independently selected from hydrogen, halogen, trihaloalkyl, alkyl having 1, 2, 3, 4 or 5 carbon atoms, electron donor groups selected from alkoxy having 1, 2, 3, 4 or 5 carbon atoms, trihaloalkoxy, hydroxy or amino, electron acceptor groups selected from cyano, sulphonic, nitro, or amide;

$R_6$, $R_7$ and $R_8$, which may be the same or different, are selected from hydrogen, halogen, trihaloalkyl, alkyl having 1, 2, 3, 4 or 5 carbon atoms, electron donor groups selected from alkoxy having 1, 2, 3, 4 or 5 carbon atoms, trihaloalkoxy, hydroxy or amino, electron acceptor groups selected from cyano, sulphonic, nitro, or amide; and $R_9$, $R_{10}$ and $R_{11}$, which may be the same or different, are selected from hydrogen, halogen, trihaloalkyl, alkyl having 1, 2, 3, 4 or 5 carbon atoms, electron donor groups selected from alkoxy having 1, 2, 3, 4 or 5 carbon atoms, trihaloalkoxy, hydroxy or amino, electron acceptor groups selected from cyano, sulphonic, nitro, or amide;

and salts thereof.

2. The compound of claim 1, wherein Z has 1 or 2 carbon atoms.

3. The compound of claim 1, wherein Z has 2 carbon atoms.

4. The compound of claim 1, wherein at least one of $R_3$, $R_4$ and $R_5$ is halogen or methyl.

5. The compound of claim 4, wherein at least one of $R_3$, $R_4$ and $R_5$ is fluoro, chloro, bromo or methyl.

6. The compound of claim 1, wherein the groups $R_3$, $R_4$ and $R_5$ are in the 2-, or 2,4-, or 2,4,6-positions relative to the point of attachment of the phenyl ring to which they are attached to the background chain.

7. The compound of claim 1, wherein trihaloalkyl is selected from trifluoromethyl.

8. The compound of claim 1 in which $R_2$ is a methylamino, dimethylamino, ethylamino or diethylamino group.

9. The racemic or optically active compound of claim 1, selected from the group consisting of:

| No. | Compound name | salt |
|---|---|---|
| 1:1 | 3-Amino-N-[(3-bromo-phenyl)-cyclohexylcarbamoyl-methyl]-N-[2-(1H-indol-3-yl)-ethyl]-propionamide | HCl |
| 1:2 | 3-Amino-N-[(2-bromo-phenyl)-cyclohexylcarbamoyl-methyl]-N-[2-(1H-indol-3-yl)-ethyl]-propionamide | HCl |
| 1:3 | 3-Amino-N-[(4-bromo-phenyl)-cyclohexylcarbamoyl-methyl]-N-[2-(1H-indol-3-yl)-ethyl]-propionamide | HCl |
| 1:4 | 3-Amino-N-[cyclohexylcarbamoyl-(2,4-dibromo-phenyl)-methyl]-N-[2-(1H-indol-3-yl)-ethyl]-propionamide | HCl |
| 1:5 | 3-Amino-N-[cyclohexylcarbamoyl-(2,5-dibromo-phenyl)-methyl]-N-[2-(1H-indol-3-yl)-ethyl]-propionamide | HCl |
| 1:6 | 3-Amino-N-[benzylcarbamoyl-(2-bromo-phenyl)-methyl]-N-[2-(1H-indol-3-yl)-ethyl]-propionamide hydrochloride | HCl |
| 1:7 | N-[Benzylcarbamoyl-(2-bromo-phenyl)-methyl]-3-dimethylamino-N-[2-(1H-indol-3-yl)-ethyl]-propionamide acetamide | |
| 1:8 | N-[Benzylcarbamoyl-(2-bromo-phenyl)-methyl]-N-[2-(5-bromo-1H-indol-3-yl)-ethyl]-3-dimethylamino-propionamide | |
| 1:9 | 3-Amino-N-[benzylcarbamoyl-(2,4-dibromo-phenyl)-methyl]-N-[2-(1H-indol-3-yl)-ethyl]-propionamide | HCl |
| 1:10 | 3-Amino-N-[benzylcarbamoyl-(2,5-dibromo-phenyl)-methyl]-N-[2-(1H-indol-3-yl)-ethyl]-propionamide | HCl |
| 1:11 | 3-Amino-N-[benzylcarbamoyl-(3-bromo-phenyl)-methyl]-N-[2-(1H-indol-3-yl)-ethyl]-propionamide | HCl |
| 1:12 | 3-Amino-N-[benzylcarbamoyl-(4-bromo-phenyl)-methyl]-N-[2-(1H-indol-3-yl)-ethyl]-propionamide | HCl |
| 1:13 | 3-Amino-N-[(2-bromo-phenyl)-phenylcarbamoyl-methyl]-N-[2-(1H-indol-3-yl)-ethyl]-propionamide | $CF_3COOH$ |
| 1:14 | 3-Amino-N-[(3-bromo-phenyl)-phenylcarbamoyl-methyl]-N-[2-(1H-indol-3-yl)-ethyl]-propionamide | $CF_3COOH$ |
| 1:15 | 3-Amino-N-[(4-bromo-phenyl)-phenylcarbamoyl-methyl]-N-[2-(1H-indol-3-yl)-ethyl]-propionamide | $CF_3COOH$ |
| 1:16 | 3-Amino-N-[(2,4-dibromo-phenyl)-phenylcarbamoyl-methyl]-N-[2-(1H-indol-3-yl)-ethyl]-propionamide | $CF_3COOH$ |

| No. | Compound name | salt |
|---|---|---|
| 1:17 | 3-Amino-N-[(2,5-dibromo-phenyl)-phenylcarbamoyl-methyl]-N-[2-(1H-indol-3-yl)-ethyl]-propionamide | CF₃COOH |
| 1:18 | N-[(2-Chloro-phenyl)-phenylcarbamoyl-methyl]-N-[2-(6-fluoro-1-indol-3-yl)-ethyl]-3-guanidino-propionamide | HCl |
| 1:19 | 3-Amino-N-[(4-fluoro-phenylcarbamoyl)-(4-trifluoromethyl-phenyl)-methyl]-N-[2-(5-methoxy-1H-indol-3-yl)-ethyl]-propionamide | |
| 1:20 | N-[(4-Chloro-3-nitro-phenyl)-phenylcarbamoyl-methyl]-3-guanidino-N-[2-(6-methoxy-1H-indol-3-yl)-ethyl]-propionamide | |
| 1:22 | 3-Amino-N-[(2-chloro-4-fluoro-phenyl)-(4-fluoro-phenylcarbamoyl)-methyl]-N-[2-(6-fluoro-1H-indol-3-yl)-ethyl]-propionamide | |
| 1:23 | 3-Amino-N-[(2-chloro-phenyl)-phenylcarbamoyl-methyl]-N-[2-(6-fluoro-1H-indol-3-yl)-ethyl]-propionamide | |
| 1:24 | N-[(4-Fluoro-phenylcarbamoyl)-(4-trifluoromethyl-phenyl)-methyl]-3-guanidino-N-[2-(5-methoxy-1H-indol-3-yl)-ethyl]-propionamide | |
| 1:25 | 3-Amino-N-[(4-chloro-3-nitro-phenyl)-phenylcarbamoyl-methyl]-N-[2-(6-methoxy-1H-indol-3-yl)-ethyl]-propionamide | |
| 1:26 | N-[(2-Chloro-4-fluoro-phenyl)-(4-fluoro-phenylcarbamoyl)-methyl]-N-[2-(6-fluoro-1H-indol-3-yl)-ethyl]-3-guanidino-propionamide | |
| 1:27 | N-[(2-Chloro-4-fluoro-phenyl)-(4-fluoro-phenylcarbamoyl)-methyl]-3-guanidino-N-[2-(5-methoxy-1H-indol-3-yl)-ethyl]-propionamide | |
| 1:28 | N-[(2-Chloro-4-fluoro-phenyl)-(4-fluoro-phenylcarbamoyl)-methyl]-3-guanidino-N-[2-(5-methoxy-1H-indol-3-yl)-ethyl]-propionamide | |
| 1:29 | 3-Amino-N-[(2-chloro-4-fluoro-phenyl)-(4-fluoro-phenylcarbamoyl)-methyl]-N-[2-(5-methoxy-1H-indol-3-yl)-ethyl]-propionamide | |
| 1:30 | N-[2-(6-Fluoro-1H-indol-3-yl)-ethyl]-N-[(4-fluoro-phenylcarbamoyl)-(4-trifluoromethyl-phenyl)-methyl]-3-guanidino-propionamide | |
| 1:31 | 3-Amino-N-[2-(6-fluoro-1H-indol-3-yl)-ethyl]-N-[(4-fluoro-phenylcarbamoyl)-(4-trifluoromethyl-phenyl)-methyl]-propionamide | |
| 1:32 | 3-Amino-N-[(2-chloro-phenyl)-phenylcarbamoyl-methyl]-N-2-(6-methoxy-1H-indol-3-yl)-ethyl]-propionamide | |
| 1:33 | N-[(2-Chloro-phenyl)-phenylcarbamoyl-methyl]-3-guanidino-N-[2-(6-methoxy-1H-indol-3-yl)-ethyl]-propionamide | |
| 1:34 | 3-Amino-N-[(4-chloro-3-nitro-phenyl)-phenylcarbamoyl-methyl]-N-[2-(6-fluoro-1H-indol-3-yl)-ethyl]-propionamide | |
| 1:35 | N-[(4-Chloro-3-nitro-phenyl)-phenylcarbamoyl-methyl]-N-[2-(6-fluoro-1H-indol-3-yl)-ethyl]-3-guanidino-propionamide | |
| 1:36 | N-[(2-Bromo-phenyl)-phenylcarbamoyl-methyl]-3-guanidino-N-[2-(1H-indol-3-yl)-ethyl]-propionamide | |
| 1:37 | 3-Amino-N-[(2-chloro-phenyl)-penylcarbamoyl-methyl]-N-[2-(1Hindol-3-yl)-ethyl]-propionamide | |
| 1:38 | N-[(2-Chloro-phenyl)-phenylcarbamoyl-methyl]-3-guanidino-N-[2-(1H-indol-3-yl)-ethyl]-propionamide | |
| 1.39 | 3-Amino-N-[(2-bromo-phenyl)-(4-fluoro-phenylcarbamoyl)-methyl]-N-[2-(1H-indol-3-yl)-propionamide | |
| 1:40 | N-[(2-Bromo-phenyl)-(4-fluoro-phenylcarbamoyl)-methyl]-3-guanidino-N-[2-(1H-indol-3-yl)-ethyl]-propionamide | |
| 1:41 | N-[(2,4-Dibromo-phenyl)-phenylcarbamoyl-methyl]-3-guanidino-N-[2-(1H-indol-3-yl)-ethyl]-propionamide | |
| 1:42 | 3-Amino-N-[(2-chloro-4-fluoro-phenyl)-phenylcarbamoyl-methyl]-N-[2-(1H-indol-3-yl)-ethyl]-propionamide | |
| 1:43 | N-[(2-Chloro-4-fluoro-phenyl)-phenylcarbamoyl-methyl]-3-guanidino-N-[2-(1H-indol-3-yl)-ethyl]-propionamide | |
| 1:44 | 3-Amino-N-[(2,4-dibromo-phenyl)-(4-fluoro-phenylcarbamoyl)-methyl]-N-[2-(1H-indol-3-yl)-ethyl]-propionamide | |
| 1:45 | N-[(2,4-Dibromo-phenyl)-(4-fluoro-phenylcarbamoyl)-methyl]-3-guanidino-N-[2-(1H-indol-3-yl)-ethyl]-propionamide | |
| 1:46 | N-[(4-Bromo-phenyl)-phenylcarbamoyl-methyl]-3-guanidino-N-[2-(1H-indol-3-yl)-ethyl]-propionamide | |
| 1:47 | 3-Amino-N-[(4-chloro-phenyl)-phenylcarbamoyl-methyl]-N-[2-(1H-indol-3-yl)-ethyl]-propionamide | |
| 1:48 | N-[(4-Chloro-phenyl)-phenylcarbamoyl-methyl]-3-guanidino-N-[2-(1H-indol-3-yl)-ethyl]-propionamide | |
| 1:49 | 3-Amino-N-[(4-chloro-phenyl)-(4-chloro-phenylcarbamoyl)-methyl]-N-[2-(1H-indol-3-yl)-ethyl]-propionamide | |
| 1:50 | N-[(4-Chloro-phenyl)-(4-chloro-phenylcarbamoyl)-methyl]-3-guanidino-N-[2-(1H-indol-3-yl)-ethyl]-propionamide | |
| 1:51 | 3-Amino-N-[(4-chloro-phenyl)-phenylcarbamoyl-methyl]-N-[2-(5-methoxy-1H-indol-3-yl)-ethyl]-propionamide | |
| 1:52 | N-[(4-Chloro-phenyl)-phenylcarbamoyl-methyl]-3-guanidino-N-[2-(5-methoxy-1H-indol-3-yl)-ethyl]-propionamide | |
| 1:53 | 3-Amino-N-[2-(1H-indol-3-yl)-ethyl]-N-(phenylcarbamoyl-o-tolyl-methyl)-propionamide | CF₃COOH |
| 1:54 | 4-Amino-N-[benzylcarbamoyl-(2-bromo-phenyl)-methyl]-N-(4-trifluoromethoxy-benzyl)butyramide | HCl |
| 1:55 | 3-Diethylamino-N-[(3-fluoro-4-methoxy-phenyl)-(4-fluoro-phenylcarbamoyl)-methyl]-N-[2-(5-methyl-1H-indol-3-yl)-ethyl]-propionamide | AcOH |
| 1:56 | 3-Guanidino-N-[2-(1H-indol-3-yl)-ethyl]-N-(phenylcarbamoyl-o-tolyl-methyl)-propionamide | |
| 1:57 | 3-Guanidino-N-[2-(1H-indol-3-yl)-ethyl]-N-[(2-methoxy-phenyl)-phenylcarbamoyl-methyl]-propionamide | |
| 1:58 | 3-Guanidino-N-[2-(1H-indol-3-yl)-ethyl]-N-[(4-methoxy-2-methyl-phenyl)-phenylcarbamoyl-methyl]-propionamide | |
| 1:59 | 3-Guanidino-N-[2-(1H-indol-3-yl)-ethyl]-N-[(4-methoxy-2,5-dimethyl-phenyl)-phenylcarbamoyl-methyl]-propionamide | |
| 1:60 | 3-Amino-N-[2-(1H-indol-3-yl)-ethyl]-N-[(2-methoxy-phenyl)phenylcarbamoyl-methyl]-propionamide | |
| 1:61 | 3-Amino-N-[2-(1H-indol-3-yl)-ethyl]-N-[(4-methoxy-2-methyl-phenyl)phenylcarbamoyl-methyl]-propionamide | |
| 1:62 | 3-Guanidino-N-[2-(1H-indol-3-yl)-ethyl]-N-[(4-methoxy-2,5-dimethyl-phenyl)-phenylcarbamoyl-methyl]-propionamide | | or a physiologically acceptable salt thereof.

10. The compound of claim 1, further comprising a label.

11. A pro-drug from which a compound of claim 1 is formed in vivo.

12. A pharmaceutical composition comprising a compound of claim 1 or a pro-drug of a compound of claim 1 formed in vivo, together with one or more pharmaceutically acceptable adjuvants, carriers, diluents or excipients.

13. A method of treating inflammation, arthritic conditions, rheumatoid arthritis, osteoarthritis, psoriatic arthritis or of inducing central nerve regeneration comprising the use or administration to a subject of a compound of claim 1 or a pro-drug of a compound of claim 1 formed in vivo.

14. The compound of claim 10, wherein the label is a radioactive label or a toxic agent.

* * * * *